(12) United States Patent
Engelhardt et al.

(10) Patent No.: US 7,132,479 B2
(45) Date of Patent: Nov. 7, 2006

(54) POLYMER MIXTURES WITH IMPROVED ODOR CONTROL

(75) Inventors: Friedrich Engelhardt, Frankfurt (DE); Rüdiger Funk, Niedernhausen (DE); Mariola Wanior, Erlensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 34 days.

(21) Appl. No.: 10/505,189

(22) PCT Filed: Mar. 4, 2003

(86) PCT No.: PCT/EP03/02183

§ 371 (c)(1),
(2), (4) Date: Aug. 19, 2004

(87) PCT Pub. No.: WO03/076514

PCT Pub. Date: Sep. 18, 2003

(65) Prior Publication Data

US 2005/0154133 A1    Jul. 14, 2005

(30) Foreign Application Priority Data

Mar. 8, 2002   (DE) ............................... 102 10 124

(51) Int. Cl.
  *C08L 35/06*   (2006.01)

(52) U.S. Cl. ..................... 525/207; 525/54.23; 525/74; 525/201; 525/937; 524/916; 502/402; 428/393; 428/394; 428/402; 428/407

(58) Field of Classification Search ............. 525/54.23, 525/74, 201, 207, 937; 502/402; 428/393, 428/394, 402, 407; 524/916
See application file for complete search history.

(56) References Cited

U.S. PATENT DOCUMENTS

| 5,645,542 A | 7/1997 | Anjur et al. |
| 5,672,419 A | 9/1997 | Mukaida et al. |
| 5,716,707 A | 2/1998 | Mukaida et al. |

FOREIGN PATENT DOCUMENTS

| EP | 0 349 240 | 1/1990 |
| EP | 0 454 497 | 10/1991 |
| JP | 02 113826 | 4/1990 |
| JP | 04004247 | 1/1992 |
| JP | 07 292023 | 11/1995 |

*Primary Examiner*—Fred Teskin
(74) *Attorney, Agent, or Firm*—Marshall, Gerstein & Borun LLP

(57) ABSTRACT

The present invention relates to polymer mixtures including hydrogel-forming polymers capable of absorbing aqueous fluids and prepared by polymerization of olefinically unsaturated carboxylic acids or derivatives thereof together with copolymers of $C_2$–$C_8$ olefins or styrenes with anhydrides and also their preparation, use and hygiene articles which include same.

12 Claims, No Drawings

POLYMER MIXTURES WITH IMPROVED ODOR CONTROL

CROSS-REFERENCE TO RELATED APPLICATION

This is the U.S. national phase application of International Application No. PCT/EPO3/02183, filed Mar. 4, 2003, which claims the benefit of German patent application No. 102 10 124.8, filed Mar. 8, 2002.

DESCRIPTIOIN

The present invention relates to polymer mixtures including hydrogel-forming polymers capable of absorbing aqueous fluids and prepared by polymerization of olefinically unsaturated carboxylic acids or derivatives thereof together with copolymers of $C_2$–$C_8$ olefins or styrenes with anhydrides and also their preparation, use in hygiene articles and hygiene articles which include same. More particularly, the invention relates to 2-component polymer mixtures of hydrogel-forming polymers with copolymers of $C_2$–$C_8$ olefins or styrenes with anhydrides.

Swellable hydrogel-forming addition polymers, known as superabsorbent polymers or SAPs, are known from the prior art. They are networks of flexible hydrophilic addition polymers, which can be both ionic and nonionic in nature. They are capable of absorbing and binding aqueous fluids by forming a hydrogel and therefore are preferentially used for manufacturing tampons, diapers, sanitary napkins, incontinence articles, training pants for children, insoles and other hygiene articles for the absorption of body fluids. Superabsorbents are also used in other fields of technology where fluids, especially water or aqueous solutions, are absorbed. These fields include for example storage, packaging, transportation (packaging material for water-sensitive articles, for example flower transportation, shock protection); food sector (transportation of fish, fresh meat; absorption of water, blood in fresh fish/meat packs); medicine (wound plasters, water-absorbent material for burn dressings or for other weeping wounds); cosmetics (carrier material for pharmaceuticals and medicaments, rheumatic plasters, ultrasound gel, cooling gel, cosmetic thickeners, sunscreen); thickeners for oil/water or water/oil emulsions; textiles (gloves, sportswear, moisture regulation in textiles, shoe inserts); chemical process industry applications (catalyst for organic reactions, immobilization of large functional molecules (enzymes), adhesive for agglomerations, heat storage media, filtration aids, hydrophilic component in polymer laminates, dispersants, liquefiers); building construction, installation (powder injection molding, clay-based renders, vibration-inhibiting medium, assistants in relation to tunneling in water-rich ground, cable sheathing); water treatment, waste treatment, water removal (de-icers, reusable sandbags); cleaning; agriculture industry (irrigation, retention of meltwater and dew precipitates, composting additive, protection of forests against fungal and insect infestation, delayed release of active ingredients to plants); fire protection (flying sparks)(covering houses or house walls with SAP gel, since water has a very high heat capacity, ignition can be prevented; spraying of SAP gel in the case of fires such as for example forest fires); coextrusion agent in thermoplastic polymers (hydrophilicization of multilayer films); production of films and thermoplastic moldings capable of absorbing water (for example agricultural films capable of storing rain and dew water; SAP-containing films for keeping fresh fruit and vegetables which can be packed in moist films; the SAP stores water released by the fruit and vegetables without forming condensation droplets and partly reemits the water to the fruit and vegetables, so that neither fouling nor wilting occurs; SAP-polystyrene coextrudates for example for food packs such as meat, fish, poultry, fruit and vegetables); carrier substance in active-ingredient formulations (drugs, crop protection). Within hygiene articles, superabsorbents are generally positioned in an absorbent core which, as well as SAP, comprises other materials, including fibers (cellulose fibers), which act as a kind of liquid buffer to intermediately store the spontaneously applied liquid insults and are intended to ensure efficient channelization of the body fluids in the absorbent core toward the superabsorbent.

The current trend in the hygiene sector, e.g. in diaper design, is toward ever thinner constructions having a reduced cellulose fiber content and an increased hydrogel content. The trend toward ever thinner diaper constructions has substantially changed the performance profile required of the water swellable hydrophilic polymers over the years. Whereas at the start of the development of highly absorbent hydrogels it was initially solely the very high swellability on which interest focused, it was subsequently determined that the ability of the superabsorbent to transmit and distribute fluid is also of decisive importance. It has been determined that conventional superabsorbents greatly swell at the surface on wetting with liquid, so that transportation of liquid into the particle interior is substantially compromised or completely prevented. This trait of superabsorbents is known as gel blocking. The greater amount of polymer per unit area in the hygiene article must not cause the swollen polymer to form a barrier layer to subsequent fluid. A product having good transportation properties will ensure optimal utilization of the entire hygiene article. This prevents the phenomenon of gel blocking, which in the extreme case will cause the hygiene article to leak. Fluid transmission and distribution is thus of decisive importance with regard to the initial absorption of body fluids.

A lot of work has been done to try to generate absorbing structures without any additions of cellulosic fibers or other nonwoven fibrous materials that ideally form even continuous hydrogel zones in order to ensure a higher loading of the absorbent core with highly absorptive hydrogel-forming polymer material.

The literature additionally includes accounts of the use of water-absorbing films which are likewise based on hydrogel-forming addition polymers but whose monomer solution is applied two-dimensionally prior to the polymerization, or else, starting from hydrogel-forming polymer particles, an intra-molecular crosslinking is carried out to form macrostructures. For instance, JP 04004247 describes the preparation of a water-absorbing film from maleic anhydride copolymer whose structural units are based on (I) alpha-olefinic or styrene units and (II) on maleic anhydride structures.

However, the use of water-absorbing films gives rise to fluid transportation problems, since insufficient diffusion times through the hydrogel compromise or even stop any fluid transmission into lower layers. The same is true of the use of hydrogel-forming polymer particles in high concentration, where the initial swell leads to mutual contact between the swollen hydrogel particles and hence to the formation of a gel-continuous zone.

Good transportation properties are possessed for example by hydrogels having high gel strength in the swollen state. Gels lacking in strength are deformable under an applied pressure, for example pressure due to the bodyweight of the wearer of the hygiene article, and clog the pores in the SAP/cellulosic fiber absorbent and so prevent continued uptake of fluid. Enhanced gel strength is generally obtained through a higher degree of crosslinking, although this reduces retention performance. As might be expected from the inherent nature of hydrogel-forming addition polymers, it has not been possible to combine properties such as high absorptive capacity and high gel strength in one product.

One way of enhancing gel strength while preserving high absorptive capacities is surface postcrosslinking. In this process, dried superabsorbents having an average crosslink density are subjected to an additional crosslinking step. The process is known to one skilled in the art and described in EP-A-0 349 240. Surface postcrosslinking increases the crosslink density in the sheath of the superabsorbent particle, whereby the absorbency under load is raised to a higher level. Whereas the absorption capacity decreases in the superabsorbent particle sheath, the core has an improved absorption capacity (compared to the sheath) owing to the presence of mobile polymer chains, so that sheath construction ensures improved fluid transmission without occurrence of the gel blocking effect. It is perfectly desirable for the total capacity of the superabsorbent to be occupied not spontaneously but with time delay. Since the hygiene article is generally repeatedly insulted with urine, the absorption capacity of the superabsorbent should sensibly not be exhausted after the first disposition. However, this leaves the problem of inadequate acquisition times, which have to be optimized particularly in those regions of the hygiene article which are exposed to the most fluid.

When hydrogels are used in the hygiene sector, they become exposed to body fluids such as urine or menses. Body fluids generally contain malodorous components of the amine or fatty acid type, which appear alongside the organic components anyhow present, for example, amines, acids, aldehydes, ketones, phenols, polycyclics, indoles, aromatics, polyaromatics, etc., that are responsible for unpleasant body odors. Odor development takes place in two stages, first in the course of exudation from the body region and then when the fluid has already been present in the absorption medium for a defined time. Both odor factors have to be eliminated, since it is undesirable for cost reasons to change the hygiene article after every absorption process.

The highly swellable hydrogels used in the hygiene sector are at present addition polymers having a degree of neutralization in the range from 60 to 80 mol %, based on the polymerized acid-functional monomer units. However, it was found in the course of the sniff test that a higher pH will generally encourage bacterial growth. In the process, the urea in the urine is increasingly split by urease into carbon dioxide and ammonia, which leads to a further increase in the pH. This in turn reinforces bacterial growth, and enzyme activity is further increased. One consequence of the raised pH is the occurrence of soft skin, making the skin more susceptible to bacterial colonization. This results directly in skin irritation which will preclude the wearing of the hygiene article for a prolonged period.

When acidic hydrogels are used in hygiene articles, odor control is good. However, there are disadvantages with existing manufacturing processes, since the polymerization of the monomer solution is very slow, so that batch operation is the only option. In addition, appreciable problems arise when it comes to dividing the fully acidic polymer gel, and the subsequent neutralization is merely diffusion-controlled, so that the polymer surface has an excess of base.

Hitherto the following possibilities have been available for attempting to achieve odor control in the hygiene sector:

Odor control coupled with simultaneous absorption by addition of inert inorganic substances having a large surface area, generally as a solid onto the surface of powders or granules for manufacturing absorbent polymers. Zeolites, active carbon, bentonites, finely divided amorphous silicas such as AEROSIL® or CAB-O-SIL® are used here.

Addition of substances capable of complexing with organic molecules or with metal ions present in the body fluid to prevent the development of unpleasant odors. This preferably takes the form of the use of cyclodextrins (any modification of unsubstituted cyclodextrins which contains from 6 to 12 glucose units, for example alpha-cyclodextrin, beta-cyclodextrin, gamma-cyclodextrin and/or derivatives and/or mixtures thereof). Mixtures of cyclodextrins are preferred, since they provide broader complexation of organic molecules over a wider molecular weight range. Cyclodextrins are used in amounts from 0.1% to about 25%, preferably from 1% to about 20%, more preferably from 2% to about 15% and especially from 3 to 10%, based on the total weight of the composition. Cyclodextrins are added in small particle size (usually less than 12 µm) to offer a large surface area for odor elimination. Further complexing agents are aminopolycarboxylic acids and their salts, ethylenediaminetetraacetate EDTA, ethylenediaminepentamethylenephosphonic acid, ethylenediaminetetramethylenephosphonic acid, aminophosphates, polyfunctional aromatics, N,N-disuccinic acid.

Masking of unpleasant odors by addition of perfumes or deodorants. These are added in free form or in encapsulated form (for example in cyclodextrins). The latter form makes it possible to release the perfume with a time delay. Nonlimiting examples of perfumes are allyl caproate, allylcyclohexane acetate, allylcyclohexane propionate, allyl heptanoate, amyl acetate, amyl propionate, anetole, anisole, benzaldehyde, benzyl acetate, benzylacetone, benzyl alcohol, benzyl butyrate, benzyl formate, benzyl isovalerate, benzyl propionate, butyl benzoate, butyl caproate, camphor, cis-3-hexenyl acetate, cis-3-hexenyl butyrate, cis-3-hexenyl caproate, cis-3-hexenyl valerate, citronellol, citronellyl derivatives, Cyclal C, cyclohexylethyl acetate, 2-decylaldehyde, dihydromyrcenol, dimethylbenzylcarbinol and derivatives thereof, dimethyloctanol, diphenyl oxide, ethyl acetate, ethyl acetoacetate, ethyl amyl ketone, ethyl benzoate, ethyl butyrate, ethyl hexyl ketone, ethyl phenylacetate, eucalyptol, fenchyl acetate, fenchyl alcohol, tricyclodecenyl acetate, tricyclodecenyl propionate, geraniol, geranyl derivatives, heptyl acetate, heptyl isobutyrate, heptyl propionate, hexenol, hexenyl acetate, hexenyl isobutyrate, hexyl acetate, hexyl formate, hexyl isobutyrate, hexyl isovalerate, hexyl neopentanoate, hydroxycitronellal, α-ionone, β-ionone, γ-ionone, isoamyl alcohol, isobornyl acetate, isobornyl propionate, isobutyl benzoate, isobutyl caproate, isononyl acetate, isononyl alcohol, isomenthol, isomenthone, isononyl acetate, isopulegol, isopulegyl acetate, isoquinoline, dodecanal, lavandulyl acetate, ligustral, δ-limonene, linalool and derivatives, menthone, menthyl acetate, methylacetophenone, methyl amyl ketone, methyl anthranilate, methyl benzoate, methyl benzylacetate, methylchavicol, methyleugenol, methylheptenone, methyl heptynecarbonate, methyl heptyl ketone, methyl hexyl ketone, methylnonylacetaldehyde, α-iso"γ"methylionone, methyloctylacetaldehyde, methyl octyl ketone, methylphenylcarbinyl acetate, methyl salicylate, myrcene, myrcenyl acetate, neral, nerol, neryl acetate, nonalactone, nonyl butyrate, nonyl alcohol, nonyl acetate, nonylaldehyde, octalactone, octyl acetate, octyl alcohol, octylaldehyde, D-limonene, p-cresol, p-cresyl methyl ether, p-cymene, p-isopropyl-p-methylacetophenone, phenethyl anthranilate, phenoxyethanol, phenylacetaldehyde, phenylethyl acetate, phenylethyl alcohol, phenylethyldimethylcarbinol, α-pinene, β-pinene, α-terpinene, γ-terpinene, terpineol, terpinyl acetate, terpinyl propionate, tetrahydrolinalool, tetrahydromyrcenol, thymol, prenyl acetate, propyl butyrate, pulegone, safrole, δ-undecalactone, γ-undecalactone, undecanal, undecyl alcohol, veratrol, verdox, vertenex, viridine.

Addition of urease inhibitors to control the formation or activity of enzymes responsible for the cleavage of urea into ammonia and hence for odor development.

Addition of antimicrobial substances. Enzymes control bacterial growth and thereby minimize odor development due to bacterial degradation processes (e.g., oxidoreductase+mediator). Examples of antimicrobial substances include quaternary ammonium compounds, phenols, amides, acids and nitro compounds and also mixtures thereof.

Examples of quaternary ammonium compounds include 2-(3-anilinovinyl)-3,4-dimethyloxazolinium iodide, alkylisoquinolium bromide, benzalkonium chloride, benzethonium chloride, cetylpyridinium chloride, chlorhexidine gluconate, chlorhexidine hydrochloride, lauryltrimethylanmonium compounds, methylbenzethonium chloride, stearyltrimethylammonium chloride, 2,4,5-trichlorophenoxide and also mixtures thereof.

Examples of phenols include benzyl alcohol, p-chlorophenol, chlorocresol, chloroxylenol, cresol, o-cymen-5-ol (BIOSOL), hexachlorophene, chinokitiol, isopropylmethylphenol, parabens (with methyl, ethyl, propyl, butyl, isobutyl, isopropyl, and/or sodium methyl substituents), phenethyl alcohol, phenol, phenoxyethanol, o-phenylphenol, resorcinol, resorcinol monoacetate, sodium parabens, sodium phenolsulfonate, thioxolone, 2,4,4'-trichloro-2'-hydroxydiphenyl ether, zinc phenolsulfonate, di-tert-butylphenol, hydroquinone, BHT and also mixtures thereof.

Examples of amides include diazolidinylurea, 2,4-imidazolidine-dione (HYDATOIN), 3,4,4'-trichlorocarbanilide, 3-trifluoro-methyl-4,4'-dichlorocarbanilide, undecylenoic acid monoethanol-amide and also mixtures thereof.

Examples of acids include benzoates, benzoic acid, citric acid, dehydroacetic acid, potassium sorbate, sodium citrates, sodium dehydroacetate, sodium salicylate, sodium salicylic acid, sorbitanic acid, undecylenoic acid, zinc undecylenate, zinc oxide, zinc phenolsulfonate, ascorbic acid, acetylsalicylic acid, salicylaldehyde, salicylic acid derivatives, adipic acid, adipic acid derivatives and also mixtures thereof.

Examples of nitro compounds include 2-bromo-2-nitro-2,3-propanediol (BRONOPOL), methyldibromoglutaronitrile and propylene glycol (MERGUARD) and also mixtures thereof.

In addition the following compounds are useful as biocides: 2,5-dimethoxytetrahydrofuran, 2,5-diethoxytetrahydrofuran, 2,5-dimethoxy-2,5-dihydrofuran, 2,5-diethoxy-2,5-dihydrofuran, succinaldehyde, glutaraldehyde, glyoxal, glyoxylic acid, hexahydrotriazine, tetrahydro-3,5-dimethyl-2H-1,3,5-thiadiazine-2-thione (Dazomet), 2,4-dichlorobenzyl alcohol, benzalkonium chloride, chlorhexidine gluconate, triclosan.

Use of transition metal compounds (Cu, Ag, Zn). Use of microcapsules which release the active substance on contact with moisture.

As well as the classes of compounds mentioned, useful odor control compounds further include the following: peroxides, bicarbonate, triclosan, plant extracts, ethereal oils, boron compounds, poly-alpha-amino acids (polylysine), imides, polyimides, PVP-iodine, use of certain polymeric substances such as chitosan, polyglycosides, oxidizing agents, cyclophanes.

In general, however, the addition of odor inhibitors will have an adverse effect on the absorption profile of superabsorbent hydrogels. Therefore, the polymer mixtures of the present invention are preferably used without these odor-inhibiting materials.

It is an object of the present invention to develop a product combining high absorptive performance and/or swell rate with odor-binding properties.

We have found that this object is achieved, surprisingly, on admixing customary hydrogel-forming addition polymers with copolymers of $C_2$–$C_8$ olefins or styrenes with anhydrides.

The present invention accordingly provides polymer mixtures including hydrogel-forming polymers capable of absorbing aqueous fluids and prepared by polymerization of olefinically unsaturated carboxylic acids or derivatives thereof (component (i)), with copolymers of $C_2$–$C_8$ olefins or styrenes with anhydrides (components(ii)). The polymer mixtures of the present invention preferably comprise granular or fibrous hydrogel-forming polymers capable of absorbing aqueous fluids and prepared by polymerization of olefinically unsaturated carboxylic acids or derivatives thereof in combination with granular or fibrous copolymers of $C_2$–$C_8$ olefins or styrenes with anhydrides. Alternatively, the copolymers of $C_2$–$C_8$ olefins or styrenes with anhydrides can also be sprayed onto the granular or fibrous hydrogel-forming polymers capable of absorbing aqueous fluids and prepared by polymerization of olefinically unsaturated carboxylic acids or derivatives thereof. The expression "granular or fibrous hydrogel-forming polymers capable of absorbing aqueous fluids and prepared by polymerization of olefinically unsaturated carboxylic acids or derivatives thereof" as used in the present invention does not comprehend copolymers of $C_2$–$C_8$ olefins or styrenes with anhydrides. The hydrogel-forming polymers capable of absorbing aqueous fluids are preferably prepared by polymerization of acrylic acid or salts thereof. These hydrogel-forming polymers capable of absorbing aqueous fluids are therefore preferably based on polyacrylate. The copolymers of $C_2$–$C_8$ olefins or styrenes with anhydrides can themselves be hydrogel-forming, for example by being partially hydrolyzed. In that case, they have preferably been hydrolyzed to 15 mol % or less. Particular preference is given to unhydrolyzed copolymers. Preference is given to polymer mixtures prepared by a process in which the hydrogel-forming polymers and the copolymer of $C_2$–$C_8$ olefins or styrenes with anhydrides are prepared in two steps and subsequently mixed in a defined ratio.

The copolymers of $C_2$–$C_8$ olefins or styrenes with anhydrides are preferably used unhydrolyzed in pulverulent (granular) form. When this copolymer is used in the hygiene sector, the anhydride component ring-opens to take up the basic components (ammonia for example) which are substantially responsible for odor development and which are formed by enzymatic processes or bacterial degradation reactions. For the purposes of the present invention, the term "anhydride component" preferably comprehends anhydrides of olefinically unsaturated di- or polycarboxylic acids, for example maleic acid substituted by one or two $C_1$–$C_6$-alkyl groups. Dicarboxylic acids are preferred. Maleic anhydride is particularly preferred. By $C_2$–$C_8$ olefins are meant unsaturated compounds containing from 2 to 8 carbon atoms. Optionally, they may also contain one or more heteroatoms such as O, N, S. The following monomers are contemplated by way of example: ethylene, propylene, isobutylene, 1-butylene, $C_1$–$C_4$-methacrylates, vinyl acetate, methyl vinyl ether, isobutyl vinyl ether, 1-hexene. The monomers can be pure or mixed. Preference is given to isobutylene and vinyl acetate. By styrenes are meant styrene and substituted styrenes. There can be for example a $C_1$–$C_6$-alkyl group on the alpha carbon and/or the benzene ring can be substituted by one or more $C_1$–$C_6$-alkyl groups and/or one or more hydroxyl groups. Styrene is preferred. The molar ratio between anhydride and olefin or styrene is generally in the range from 3:1 to 1:3, preferably in the range from 2.5:1 to 1:2.5, more preferably in the range from 2:1 to 1:2 and especially 1:1. If there is an excess of one component, an excess of anhydride is preferred. The copolymers with maleic anhydride and isobutylene, diisobutylene, ethylene or styrene, all optionally with addition of vinyl acetate, are particularly preferred.

It has also been determined that, surprisingly, the addition of granular or fibrous copolymers of $C_2$–$C_8$ olefins or styrenes with anhydrides to the hydrogel-forming polymers of the prior art substantially increases the permeability.

The hydrogel-forming polymers capable of absorbing aqueous fluids can also be admixed with monomer solution or polymer solution of $C_2$–$C_8$ olefins or styrenes with anhydrides. Useful solvents include inert solvents such as acetone, DMSO, dioxane, ethyl acetate, chloroform and toluene. The monomer or polymer solutions can be sprayed onto the hydrogels and, if appropriate, subjected to a precipitation polymerization. The solvent is advantageously removed by drying at from 20 to 120° C.

The molar masses of the copolymers are generally in the range from 500 to 1 million and preferably in the range from 1 000 to 250 000.

The fraction of hydrogel-forming polymer particles exhibits a high absorptive capacity coupled with good swell rate, while the obtention of the anhydride units ensures the buffering of the fraction of basic components, for example of the ammonia fraction. The addition of copolymers of $C_2$–$C_8$ olefins or styrenes with anhydrides, moreover, provides improved permeability.

In a preferred embodiment of the present invention, the hydrogel-forming polymers are admixed with fibrous copolymers of $C_2$–$C_8$ olefins or styrenes with anhydrides. To permit spinning, the copolymer of $C_2$–$C_8$ olefins or styrenes with anhydrides is partially hydrolyzed. Such partially neutralized copolymers of $C_2$–$C_8$ olefins or styrenes with anhydrides are described for example in U.S. Pat. No. 5,026,784. According to this reference, an aqueous, fiberizable copolymer solution is obtained from (column 3, line 6) a) partially neutralized $C_2$–$C_8$ olefin-anhydride, especially maleic anhydride, copolymer having a degree of neutralization in the range from 0.2 to about 0.8 equivalent of carboxyl group units with b) from 0.1 to 10 parts by weight of at least one reactive component per 100 parts by weight of partially neutralized polymer dissolved in aqueous fluid. The reactive component is a water-soluble component bearing one amino group and at least one hydroxyl group. The reaction product has an ionic ammonium carboxylate bond formed by unneutralized carboxyl groups on the polymer and the amino group on the reactive substance.

After spinning, the fibers are heated to 140–210° C. to cure them by removing water and crosslinking through ester and amide linkages. The fibers thus crosslinked are water swellable and hence absorbent.

The addition of partially neutralized copolymers of $C_2$–$C_8$ olefins or styrenes with anhydrides in fiber form can provide higher acquisition rates and higher retention values than is the case with the granular polymer mixture of the present invention. A partial hydrolysis consumes anhydride groups and therefore generally either more copolymer is used and/or known odor inhibitors are added. The degree of partial hydrolysis is preferably not more than 15 mol %.

A particularly preferred embodiment of the present invention accordingly concerns polymer mixtures including hydrogel-forming polymers capable of absorbing aqueous fluids and prepared by polymerization of olefinically unsaturated carboxylic acids or their derivatives with copolymers of $C_2$–$C_8$ olefins or styrenes with anhydrides (granular or by spraying) and also partially hydrolyzed $C_2$–$C_8$ olefin-anhydride, especially maleic anhydride, copolymer fibers.

The polymer mixtures can be mixtures of dry hydrogel-forming polymers capable of absorbing aqueous fluids and preparable by polymerization of olefinically unsaturated carboxylic acids or derivatives thereof with dry granular copolymers of $C_2$–$C_8$ olefins or styrenes with anhydrides. The former can also have a residual water content which is lower than their respective CRC. The residual moisture content is preferably lower than the intrinsic weight of the superabsorbent, more preferably lower than 30% by weight of residual moisture, especially less than 10% by weight of residual moisture. Olefinically unsaturated carboxylic acids are preferably monoethylenically unsaturated monomers. The term "derivatives thereof" comprehends salts, esters, for example $C_1$–$C_6$-alkyl esters, anhydrides, etc, which are hydrolyzable to the free acids.

Preferred polymer mixtures are characterized in that they are pulverulent mixtures of hydrogel-forming polymers capable of absorbing aqueous fluids (component (i)) with copolymers of $C_2$–$C_8$ olefins or styrenes with anhydrides (component (ii)).

Preference is likewise given to polymer mixtures wherein the component (i) is present in a fraction in the range from 99.7% by weight to 85% by weight and the component (ii) is present in a fraction in the range from 0.3% by weight to 15% by weight, especially those wherein component (ii) is present in a fraction in the range from 0.5% by weight to 10% by weight, ie for example in 9%, 8%, 7%, 6%, 5%, 4%, 3%, 2%, 1% by weight or in between weight percentages. The remaining component or components then add to make 100% by weight in each case.

In a particularly preferred embodiment of the present invention, component (ii) comprises mixtures of granular $C_2$–$C_8$ olefin-anhydride, especially maleic anhydride, copolymer and $C_2$–$C_8$ olefin-anhydride, especially maleic anhydride, copolymer fibers capable of absorbing aqueous fluids.

Preference is likewise given to polymer mixtures wherein granular $C_2$–$C_8$ olefin-anhydride, especially maleic anhydride, copolymer (A) and $C_2$–$C_8$ olefin-anhydride, especially maleic anhydride, copolymer fibers (B) capable of absorbing aqueous fluids are present as the two constituents of component (ii) in a constituent (A) fraction of from 50% by weight to 90% by weight and a constituent (B) fraction of from 10% by weight to 50% by weight or a weight percentage in between. The remaining component or components then combine in each case with the two main constituents to add up to 100% by weight.

The polymer mixtures mentioned can be characterized in that, according to application, the components of the mixture are prepared from particles of the same or different particle size fraction. They are preferably of the same particle size fraction.

The individual components are mixed after the optional surface postcrosslinking of component (i).

The present invention also discloses various applications for the polymer mixtures as an absorbent for aqueous fluids, dispersions and emulsions, especially various hygiene article constructions containing the above polymer mixtures. Particular preference is given to the use of the polymer mixtures of the present invention as an absorbent for aqueous fluids that provides reduced odor formation. Reduced odor formation means that the addition of the copolymers at 10% by weight improves the buffering capacity by at least 0.2 pH unit, preferably at least 0.5 pH unit, more preferably at least 0.7 pH unit and especially at least 1.0 pH unit.

Methods of Making

Hydrogel-Forming Polymers

The water-swellable hydrophilic hydrogel-forming polymers are generally prepared by free-radical polymerization in an aqueous solution which includes the monomers and also, if appropriate, grafting base and crosslinkers.

Monomers Used

Hydrogel-forming polymers are in particular polymers of (co)polymerized hydrophilic monomers, graft (co)polymers of one or more hydrophilic monomers on a suitable grafting base, crosslinked cellulose or starch ethers, crosslinked carboxymethylcellulose, partially crosslinked polyalkylene oxide or natural products that swell in aqueous fluids, for example guar derivatives, alginates and carrageenans.

Suitable grafting bases can be of natural or synthetic origin. Examples are starch, cellulose or cellulose derivatives, such as carboxymethylcellulose, and also other polysaccharides and oligosaccharides, polyvinyl alcohol, polyalkylene oxides, especially polyethylene oxides and polypropylene oxides, polyamines, polyamides and also hydrophilic polyesters. Suitable polyalkylene oxides have for example the formula $R^1$—O—$(CH_2$—CHX—O$)_n$—$R^2$ where $R^1$ and $R^2$ are independently hydrogen, alkyl, alkenyl or aryl, x is hydrogen or methyl and n is an integer from 1 to 10 000.

$R^1$ and $R^2$ are each preferably hydrogen, $(C_1-C_4)$-alkyl, $(C_2-C_6)$-alkenyl or phenyl.

Preferred hydrogel-forming polymers are crosslinked polymers having acid groups which are predominantly in the form of their salts, generally alkali metal or ammonium salts. Such polymers swell particularly strongly on contact with aqueous fluids to form gels.

Preference is given to polymers which are obtained by crosslinking polymerization or copolymerization of acid-functional monoethylenically unsaturated monomers or derivatives thereof, eg salts, esters, anhydrides. It is further possible to (co)polymerize these monomers without crosslinker and to crosslink them subsequently.

Examples of such monomers bearing acid groups are monoethylenically unsaturated $C_3$- to $C_{25}$-carboxylic acids or anhydrides such as acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. It is also possible to use monoethylenically unsaturated sulfonic or phosphonic acids, for example vinylsulfonic acid, allylsulfonic acid, sulfoethyl acrylate, sulfo methacrylate, sulfopropyl acrylate, sulfopropyl methacrylate, 2-hydroxy-3-acryloyloxypropylsulfonic acid, 2-hydroxy-3-methacryloyloxypropylsulfonic acid, vinylphosphonic acid, allylphosphonic acid, styrenesulfonic acid and 2-acrylamido-2-methylpropanesulfonic acid. The monomers may be used alone or mixed.

Preferred monomers used are acrylic acid, methacrylic acid, vinylsulfonic acid, acrylamidopropanesulfonic acid or mixtures thereof, for example mixtures of acrylic acid and methacrylic acid, mixtures of acrylic acid and acrylamidopropanesulfonic acid or mixtures of acrylic acid and vinylsulfonic acid.

To optimize properties, it can be sensible to use additional monoethylenically unsaturated compounds which do not bear an acid group but are copolymerizable with the monomers bearing acid groups. Such compounds include for example the amides and nitriles of monoethylenically unsaturated carboxylic acids, for example acrylamide, methacrylamide and N-vinylformamide, N-vinylacetamide, N-methyl-N-vinylacetamide, acrylonitrile and methacrylonitrile. Examples of further suitable compounds are vinyl esters of saturated $C_1$- to $C_4$-carboxylic acids such as vinyl formate, vinyl acetate or vinyl propionate, alkyl vinyl ethers having at least 2 carbon atoms in the alkyl group, for example ethyl vinyl ether or butyl vinyl ether, esters of monoethylenically unsaturated $C_3$- to $C_6$-carboxylic acids, for example esters of monohydric $C_1$- to $C_{18}$-alcohols and acrylic acid, methacrylic acid or maleic acid, monoesters of maleic acid, for example methyl hydrogen maleate, N-vinyllactams such as N-vinylpyrrolidone or N-vinylcaprolactam, acrylic and methacrylic esters of alkoxylated monohydric saturated alcohols, for example of alcohols having from 10 to 25 carbon atoms which have been reacted with from 2 to 200 mol of ethylene oxide and/or propylene oxide per mole of alcohol, and also monoacrylic esters and monomethacrylic esters of polyethylene glycol or polypropylene glycol, the molar masses ($M_n$) of the polyalkylene glycols being up to 2 000, for example. Further suitable monomers are styrene and alkyl-substituted styrenes such as ethylstyrene or tert-butylstyrene.

These monomers without acid groups may also be used in mixture with other monomers, for example mixtures of vinyl acetate and 2-hydroxyethyl acrylate in any proportion. These monomers without acid groups are added to the reaction mixture in amounts within the range from 0 to 50% by weight, preferably less than 20% by weight.

Preference is given to crosslinked polymers of monoethylenically unsaturated monomers which bear acid groups and which are optionally converted into their alkali metal or ammonium salts before or after polymerization and of 0–40% by weight, based on their total weight, of monoethylenically unsaturated monomers which do not bear acid groups.

Preference is given to crosslinked polymers of monoethylenically unsaturated $C_3$- to $C_{12}$-carboxylic acids and/or their alkali metal or ammonium salts. Preference is given in particular to crosslinked polyacrylic acids where 5–30 mol %, preferably 5–20 mol % and particularly preferably 5–10 mol % of their acid groups, based on the monomers containing acid groups, are present as alkali metal or ammonium salts.

Possible crosslinkers include compounds containing at least two ethylenically unsaturated double bonds. Examples of compounds of this type are N,N'-methylenebisacrylamide, polyethylene glycol diacrylates and polyethylene glycol dimethacrylates each derived from polyethylene glycols having a molecular weight of from 106 to 8 500, preferably from 400 to 2 000, trimethylolpropane triacrylate, ethoxylated trimethylolpropane triacrylate (ETMPTA) especially ETMPTA ethoxylated with 15 EO on average, trimethylolpropane trimethacrylate, ethylene glycol diacrylate, ethylene glycol dimethacrylate, propylene glycol diacrylate, propylene glycol dimethacrylate, butanediol diacrylate, butanediol dimethacrylate, hexanediol diacrylate, hexanediol dimethacrylate, allyl methacrylate, diacrylates and dimethacrylates of block copolymers of ethylene oxide and propylene oxide, polyhydric alcohols, such as glycerol or pentaerythritol, doubly or more highly esterified with acrylic acid or methacrylic acid, triallylamine, dialkyldiallylammonium halides such as dimethyldiallylammonium chloride and diethyldiallylammonium chloride, tetraallylethylenediamine, divinylbenzene, diallyl phthalate, polyethylene glycol divinyl ethers of polyethylene glycols having a molecular weight of from 106 to 4 000, trimethylolpropane diallyl ether, butanediol divinyl ether, pentaerythritol triallyl ether, reaction products of 1 mol of ethylene glycol diglycidyl ether or polyethylene glycol diglycidyl ether with 2 mol of pentaerythritol triallyl ether or allyl alcohol, and/or divinylethyleneurea. Preference is given to using water-soluble crosslinkers, for example N,N'-methylenebisacrylamide, polyethylene glycol diacrylates and polyethylene glycol dimethacrylates derived from addition products of from 2 to 400 mol of ethylene oxide with 1 mol of a diol or polyol, vinyl ethers of addition products of from 2 to 400 mol of ethylene oxide with 1 mol of a diol or polyol, ethylene glycol diacrylate, ethylene glycol dimethacrylate or triacrylates and trimethacrylates of addition products of from 6 to 20 mol of ethylene oxide with 1 mol of glycerol, pentaerythritol triallyl ether and/or divinylurea.

Possible crosslinkers also include compounds containing at least one polymerizable ethylenically unsaturated group and at least one further functional group. The functional group of these crosslinkers has to be capable of reacting with the functional groups, essentially the acid groups, of the monomers. Suitable functional groups include for example hydroxyl, amino, epoxy and aziridino groups. Useful are for example hydroxyalkyl esters of the abovementioned monoethylenically unsaturated carboxylic acids, e.g., 2-hydroxyethyl acrylate, hydroxypropyl acrylate, hydroxybutyl acrylate, hydroxyethyl methacrylate, hydroxypropyl methacrylate and hydroxybutyl methacrylate, allylpiperidinium bromide, N-vinylimidazoles, for example N-vinylimidazole, 1-vinyl-2-methylimidazole and N-vinylimidazolines such as N-vinylimidazoline, 1-vinyl-2-methylimidazoline, 1-vinyl-2-ethylimidazoline or 1-vinyl-2-propylimidazoline, which can be used in the form of the free bases, in quaternized form or as salt in the polymerization. It is also possible to use dialkylaminoethyl acrylate and dimethylaminoethyl methacrylate, diethylaminoethyl acrylate and diethylaminoethyl methacrylate. The basic esters are preferably used in quaternized form or as salt. It is also possible to use glycidyl(meth)acrylate, for example.

Useful crosslinkers further include compounds containing at least two functional groups capable of reacting with the functional groups, essentially the acid groups, of the monomers. Suitable functional groups were already mentioned above, ie, hydroxyl, amino, epoxy, isocyanato, ester, amido and aziridino groups. Examples of such crosslinkers are ethylene glycol, diethylene glycol, triethylene glycol, tetraethylene glycol, polyethylene glycol, glycerol, polyglycerol, triethanolamine, propylene glycol, polypropylene glycol, block copolymers of ethylene oxide and propylene oxide, ethanolamine, sorbitan fatty acid esters, ethoxylated sorbitan fatty acid esters, trimethylolpropane, pentaerythritol, 1,3-butanediol, 1,4-butanediol, polyvinyl alcohol, sorbitol, starch, polyglycidyl ethers such as ethylene glycol diglycidyl ether, polyethylene glycol diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris[3-(1-aziridinyl)propionate], 1,6-hexamethylenediethyleneurea, diphenylmethanebis-4,4'-N,N'-diethyleneurea, haloepoxy compounds such as epichlorohydrin and α-methylepifluorohydrin, polyisocyanates such as 2,4-toluylene diisocyanate and hexamethylene diisocyanate, alkylene carbonates such as 1,3-dioxolan-2-one and 4-methyl-1,3-dioxolan-2-one, also bisoxazolines and oxazolidones, polyamidoamines and also their reaction products with epichlorohydrin, also polyquaternary amines such as condensation products of dimethylamine with epichlorohydrin, homo- and copolymers of diallyldimethylammonium chloride and also homo- and copolymers of dimethylaminoethyl(meth)acrylate which are optionally quaternized with, for example, methyl chloride.

Useful crosslinkers further include multivalent metal ions capable of forming ionic crosslinks. Examples of such crosslinkers are magnesium, calcium, barium and aluminum ions. These crosslinkers are used for example as hydroxides, carbonates or bicarbonates. Useful crosslinkers further include multifunctional bases likewise capable of forming ionic crosslinks, for example polyamines or their quaternized salts. Examples of polyamines are ethylenediamine, diethylenetriamine, triethylenetetramine, tetraethylenepentamine, pentaethylenehexamine and polyethyleneimines and also polyamines having molar masses in each case of up to 4 000 000.

The crosslinkers are present in the reaction mixture for example from 0.001 to 20% and preferably from 0.01 to 14% by weight, based on monomer.

Free Radical Polymerization

The polymerization is initiated in the generally customary manner, by means of an initiator. But the polymerization may also be initiated by electron beams acting on the polymerizable aqueous mixture. However, the polymerization may also be initiated in the absence of initiators of the abovementioned kind, by the action of high energy radiation in the presence of photoinitiators. Useful polymerization initiators include all compounds which decompose into free radicals under the polymerization conditions, for example peroxides, hydroperoxides, hydrogen peroxides, persulfates, azo compounds and redox catalysts. The use of water-soluble initiators is preferred. In some cases it is advantageous to use mixtures of different polymerization initiators, for example mixtures of hydrogen peroxide and sodium peroxodisulfate or potassium peroxodisulfate. Mixtures of hydrogen peroxide and sodium peroxodisulfate may be used in any proportion. Examples of suitable organic peroxides are acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl)peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetylcyclohexylsulfonyl peroxide, dilauryl peroxide, dibenzoyl peroxide and tert-amyl perneodecanoate. Particularly suitable polymerization initiators are water-soluble azo initiators, e.g., 2,2'-azobis(2-amidino-propane) dihydrochloride, 2,2'-azobis(N,N'-dimethylene)-isobutyramidine dihydrochloride, 2-(carbamoylazo)isobutyro-nitrile, 2,2'-azobis[2-(2'-imidazolin-2-yl)propane]dihydrochloride and 4,4'-azobis(4-cyanovaleric acid). The polymerization initiators mentioned are used in customary amounts, for example in amounts of from 0.01 to 5%, preferably from 0.05 to 2.0%, by weight, based on the monomers to be polymerized.

Useful initiators also include redox catalysts. In redox catalysts, the oxidizing component is at least one of the above-specified per compounds and the reducing component is for example ascorbic acid, glucose, sorbose, ammonium or alkali metal bisulfite, sulfite, thiosulfate, hyposulfite, pyrosulfite or sulfide, or a metal salt, such as iron(II) ions or sodium hydroxymethylsulfoxylate. The reducing component in the redox catalyst is preferably ascorbic acid or sodium sulfite. Based on the amount of monomers used in the polymerization, from $3\times10^{-6}$ to 1 mol % may be used for the reducing component of the redox catalyst system and from 0.001 to 5.0 mol % for the oxidizing component of the redox catalyst, for example.

When the polymerization is initiated using high energy radiation, the initiator used is customarily a photoinitiator. Photoinitiators include for example α-splitters, H-abstracting systems or else azides. Examples of such initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds such as the abovementioned free-radical formers, substituted hexaarylbisimidazoles or acylphosphine oxides. Examples of azides are:
2-(N,N-dimethylamino)ethyl 4-azidocinnamate,
2-(N,N-dimethylamino)ethyl 4-azidonaphthyl ketone,
2-(N,N-dimethylamino)ethyl 4-azidobenzoate, 5-azido-1-naphthyl
2'-(N,N-dimethylamino)ethyl sulfone, N-(4-sulfonylazidophenyl)-maleimide, N-acetyl-4-sulfonylazidoaniline, 4-sulfonyl-azidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcyclohexanone.
Photoinitiators, if used, are customarily used in amounts of from 0.01 to 5% of the weight of the monomers to be polymerized.

The crosslinked polymers are preferably used in partially neutralized form. The degree of neutralization is preferably in the range from 5 to 60 mol %, more preferably in the range from 10 to 40 mol %, particularly preferably in the range from 20 to 30 mol %, based on the monomers containing acid groups. Useful neutralizing agents include alkali metal bases or ammonia/amines. Preference is given to the use of aqueous sodium hydroxide solution, aqueous potassium hydroxide solution or lithium hydroxide. However, neutralization may also be effected using sodium carbonate, sodium bicarbonate, potassium carbonate or potassium bicarbonate or other carbonates or bicarbonates or ammonia. Moreover primary, secondary and tertiary amines may be used.

Alternatively, the degree of neutralization can be set before, during or after the polymerization in all apparatuses suitable for this purpose. The neutralization can be effected for example in a kneader used for the polymerization. The varying degree of neutralization entails different pH values on the part of the polymers.

Industrial processes useful for making these products include all processes which are customarily used to make superabsorbents, as described for example in Chapter 3 of "Modern Superabsorbent Polymer Technology", F. L. Buchholz and A. T. Graham, Wiley-VCH, 1998.

Polymerization in aqueous solution is preferably conducted as a gel polymerization. It involves 10–70% strength by weight aqueous solutions of the monomers and optionally of a suitable grafting base being polymerized in the presence of a free-radical initiator by utilizing the Trommsdorff-Norrish effect.

The polymerization reaction may be carried out at from 0 to 150° C., preferably at from 10 to 100° C., not only at atmospheric pressure but also at superatmospheric or reduced pressure. As is customary, the polymerization may also be conducted in a protective gas atmosphere, preferably under nitrogen.

By subsequently heating the polymer gels at from 50 to 130° C., preferably at from 70 to 100° C., for several hours, the performance characteristics of the polymers can be further improved.

Surface Postcrosslinking

Preference is given to hydrogel-forming polymers which have been surface-postcrosslinked. Surface postcrosslinking may be carried out in a conventional manner using dried, ground and classified polymer particles.

To effect surface postcrosslinking, compounds capable of reacting with the functional groups of the polymers by crosslinking are applied to the surface of the hydrogel particles, preferably in the form of an aqueous solution. The aqueous solution may contain water-miscible organic solvents. Suitable solvents are alcohols such as methanol, ethanol, i-propanol ethylene glycol, propylene glycol or acetone.

The subsequent crosslinking reacts polymers which have been prepared by the polymerization of the abovementioned monoethylenically unsaturated acids and optionally monoethylenically unsaturated comonomers and which have a molecular weight of greater than 5 000, preferably greater than 50 000, with compounds which have at least two groups reactive toward acid groups. This reaction can take place at room temperature or else at elevated temperatures up to 220° C.

Suitable postcrosslinkers include for example:
di- or polyglycidyl compounds such as diglycidyl phosphonates or ethylene glycol diglycidyl ether, bischlorohydrin ethers of polyalkylene glycols,
alkoxysilyl compounds,
polyaziridines, aziridine compounds based on polyethers or substituted hydrocarbons, for example bis-N-aziridinomethane,
polyamines or polyamidoamines and their reaction products with epichlorohydrin,
polyols such as ethylene glycol, 1,2-propanediol, 1,4-butanediol, glycerol, methyltriglycol, polyethylene glycols having an average molecular weight $M_w$ of 200–10 000, di- and polyglycerol, pentaerythritol, sorbitol, the ethoxylates of these polyols and their esters with carboxylic acids or carbonic acid such as ethylene carbonate or propylene carbonate, carbonic acid derivatives such as urea, thiourea, guanidine, dicyandiamide, 2-oxazolidinone and its derivatives, bisoxazoline, polyoxazolines, di- and polyisocyanates, di- and poly-N-methylol compounds such as, for example, methylenebis(N-methylolmethacrylamide) or melamine-formaldehyde resins, compounds having two or more blocked isocyanate groups such as, for example, trimethylhexamethylene diisocyanate blocked with 2,2,3,6-tetramethylpiperidin-4-one.

If necessary, acidic catalysts may be added, for example p-toluenesulfonic acid, phosphoric acid, boric acid or ammonium dihydrogenphosphate.

Particularly suitable postcrosslinkers are di- or polyglycidyl compounds such as ethylene glycol diglycidyl ether, the reaction products of polyamidoamines with epichlorohydrin and 2-oxazolidinone.

The crosslinker solution is preferably applied to the particles by spraying with a solution of the crosslinker in conventional reaction mixers or mixing and drying equipment such as Patterson-Kelly mixers, DRAIS turbulence mixers, Lödige mixers, screw mixers, plate mixers, fluidized bed mixers and Schugi Mix. The spraying of the crosslinker solution may be followed by a heat treatment step, preferably in a downstream dryer, at from 80 to 230° C., preferably 80–190° C., particularly preferably at from 100 to 160° C., for from 5 minutes to 6 hours, preferably from 10 minutes to 2 hours, particularly preferably from 10 minutes to 1 hour, during which not only cracking products but also solvent fractions can be removed. But the drying may also take place in the mixer itself, by heating the jacket or by blowing in a preheated carrier gas.

In a particularly preferred embodiment of the invention, the hydrophilicity of the particle surface of the hydrogel-forming polymer is additionally modified by formation of complexes. The formation of complexes on the outer shell of the hydrogel particles is effected by spraying with solutions of divalent or more highly valent metal salt solutions, and the metal cations can react with the acid groups of the polymer to form complexes. Examples of divalent or more highly valent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$, and $Au^{+/3+}$, preferred metal cations are $Mg^{2+}$, $Ca^{2+}$, $Al^{3+}$, $Ti^{4+}$, $Zr^{4+}$ and $La^{3+}$, and particularly preferred metal cations are $Al^{3+}$, $Ti^{4+}$ and $Zr^{4+}$. The metal cations may be used not only alone but also mixed with each other. Of the metal cations mentioned, all metal salts are suitable that possess adequate solubility in the solvent to be used. Of particular suitability are metal salts with weakly complexing anions such as for example chloride, nitrate and sulfate. Useful solvents for the metal salts include water, alcohols, DMF, DMSO and also mixtures thereof. Particular preference is given to water and water-alcohol mixtures such as for example water-methanol or water-1,2-propanediol.

The spraying of the metal salt solution onto the particles of the hydrogel-forming polymer may be effected not only before but also after the surface postcrosslinking of the particles. In a particularly preferred process, the spraying of the metal salt solution takes place in the same step as the spraying of the crosslinker solution, the two solutions being sprayed separately in succession or simultaneously via two nozzles or the crosslinker and metal salt solutions may be sprayed conjointly through a single nozzle.

Optionally, the hydrogel-forming polymers may be further modified by admixture of finely divided inorganic solids, for example silica, alumina, titanium dioxide and iron(II) oxide, to further augment the effects of the surface aftertreatment. Particular preference is given to the admixture of hydrophilic silica or of alumina having an average primary particle size of from 4 to 50 nm and a specific surface area of 50–450 m²/g. The admixture of finely divided inorganic solids preferably takes place after the surface modification through crosslinking/complexing, but may also be carried out before or during these surface modifications.

The surface-postcrosslinked material is generally heat treated.

Heat treatment jacket temperature: 120–180° C., preferably 140–160° C., especially 150° C.; heat treatment residence time has to be conformed to the temperature, higher temperatures involving shorter residence times and longer residence times giving rise to more pronounced postcrosslinking. Typical values are 150–10 minutes.

AUL and CRC can be optimized by controlling the postcrosslinking time.

Copolymers of $C_2$–$C_8$ olefins or styrenes with anhydrides.

Copolymers of $C_2$–$C_8$ olefins or styrenes with anhydrides are known and commercially obtainable. Their preparation has been exhaustively described, for example in U.S. Pat. No. 5,066,742 and U.S. Pat. No. 5,026,784, whose method of making is hereby incorporated into the present invention by reference.

Properties of Polymer Mixtures According to the Present Invention

The hydrogel-forming polymers capable of absorbing aqueous fluids have a particle size distribution which is generally in the range from 10 µm to about 1 000 µm, preferably in the range from about 100 µm to about 850 µm and especially in the range from 150 µm to about 700 µm. The size window mentioned preferably includes more than 80% by weight and especially more than 90% by weight of the particles.

The odor-binding copolymers of $C_2$–$C_8$ olefins or styrenes with anhydrides have a particle size distribution which is generally in the range from 10 µm to about 600 µm, preferably in the range from about 100 µm to about 400 µm and especially in the range from 150 µm to about 300 µm. The size window mentioned preferably includes more than 80% by weight and especially more than 90% by weight of the particles.

The $C_2$–$C_8$ olefin-anhydride, especially maleic anhydride, copolymer fibers capable of absorbing aqueous fluids are preferably obtained by the method of U.S. Pat. No. 5,026,784 example 1 column 8 line 24 and have the properties described there (degree of neutralization 55%, diameter of noncrosslinked fiber: 2–3 denier).

The polymer mixtures comprise improved odor control properties as well as high ultimate absorption capacity, high gel strength and permeability and also high retention. Owing to the presence of copolymers of $C_2$–$C_8$ olefins or styrenes with anhydrides, the products of the present invention have antimicrobial properties, thereby providing an odor control system which obviates the addition of further odor-inhibiting substances or odor-masking materials.

The addition of partially neutralized copolymers of $C_2$–$C_8$ olefins or styrenes with anhydrides in fiber form provides higher acquisition rates and also higher retention values than is the case with the granular polymer mixture of the present invention.

In contrast to the prior art, where an added odor control unit to the superabsorbent polymer leads to a decrease in the absorptive performance, the polymer mixture of the present invention has no adverse effect on the absorption profile. Moreover, the products of the invention permit substantially less costly manufacture, since there is no need for binders or other aids for binding an odor control unit to hydrogel-forming polymers.

The high absorptive performance and an unchanged absorptive profile on the part of the hydrogel-forming polymers used permits longer wear times when the products of the present invention are used in a hygiene article. Skin sensitization and irritation is completely avoided and eliminated by a constant pH medium.

Deployment and Use of the Polymer Mixture

The present invention further provides for the use of the abovementioned polymer mixtures in hygiene articles comprising
(A) a liquid pervious topsheet
(B) a liquid impervious backsheet
(C) a core positioned between (A) and (B) and comprising
10–100% by weight of the polymer mixture according to the invention
0–90% by weight of hydrophilic fiber material preferably 20–100% by weight of the polymer mixture according to the invention, 0–80% by weight of the hydrophilic fiber material
more preferably 30–100% by weight of the polymer mixture according to the invention, 0–70% by weight of the hydrophilic fiber material
even more preferably 40–100% by weight of the polymer mixture according to the invention, 0–60% by weight of the hydrophilic fiber material
much more preferably 50–100% by weight of the polymer mixture according to the invention, 0–50% by weight of the hydrophilic fiber material
particularly preferably 60–100% by weight of the polymer mixture according to the invention, 0–40% by weight of the hydrophilic fiber material
especially preferably 70–100% by weight of the polymer mixture according to the invention, 0–30% by weight of the hydrophilic fiber material
extremely preferably 80–100% by weight of the polymer mixture according to the invention, 0–20% by weight of the hydrophilic fiber material
most preferably 90–100% by weight of the polymer mixture according to the invention, 0–10% by weight of the hydrophilic fiber material
(D) optionally a tissue layer positioned directly above and below said core (C) and
(E) optionally an acquisition layer positioned between (A) and (C).

The hydrophilic fiber material can be wholly or partly replaced by fiber material composed of copolymers of $C_2$–$C_8$ olefins or styrenes with anhydrides. The preferred percentages are to be understood so that in the case of 10–100% by weight 11, 12, 13, 14, 15, 16, 17, 18, 19 up to in each case 100% by weight of polymer mixture according to the invention and all in between % ages (for example 12.2%) are possible and correspondingly hydrophilic fiber material from 0 to respectively 89, 88, 87, 86, 85, 83, 82, 81% by weight and in between percentages (for example 87.8%) are possible. If further materials are present in the core, the percentages of polymer and fiber decrease accordingly. The same applies to the preferred ranges, for example in the case of extremely preferably 81, 82, 83, 84, 85, 86, 87, 88, 89% by weight can be present for the polymer mixture according to the invention and correspondingly 19, 18, 17, 16, 15, 14, 13, 12, 11% by weight of the fiber material. So the preferred range contains 20, 21, 22, 23, 24, 25, 26, 27, 28, 29 to 100% by weight of the polymer mixture according to the invention, the more preferred range 30, 31, 32, 33, 34, 35, 36, 37, 38, 39 to 100% by weight of the polymer mixture according to the invention, the even more preferred range 40, 41, 42, 43, 44, 45, 46, 47, 48, 49 to 100% by weight of polymer mixture according to the invention, the much more preferred range 50, 51, 52, 53, 54, 55, 56, 57, 58, 59 to 100% by weight of polymer mixture according to the invention, the particularly preferred range 60, 61, 62, 63, 64, 65, 66, 67, 68, 69 to 100% by weight of polymer mixture according to the invention, the especially preferred range 70, 71, 71, 72, 73, 74, 75, 76, 77, 78, 79 to 100% by weight of polymer mixture according to the invention and the most preferred range 90, 91, 92, 93, 94, 95, 96, 97, 98, 99 or 100% by weight of polymer mixture according to the invention.

Hygiene articles for the purposes of the present invention include not only incontinence pads and incontinence briefs for adults but also diapers for infants.

The liquid pervious topsheet (A) is the layer which is in direct contact with the skin of the wearer. Its material comprises customary synthetic or manufactured fibers or films of polyesters, polyolefins, rayon or natural fibers such as cotton. In the case of non-woven materials the fibers are generally joined together by binders such as polyacrylates. Preferred materials are polyesters, rayon or blends thereof, polyethylene and polypropylene. Examples of liquid pervious layers are described in WO 99/57355 A1, EP 102 388 3 A2.

The liquid impervious layer (B) is generally a sheet of polyethylene or polypropylene.

The core (C) includes not only the polymer mixture of the invention but also hydrophilic fiber material. By hydrophilic is meant that aqueous fluids spread quickly over the fiber. The fiber material is usually a cellulose, modified cellulose, rayon, polyester such as polyethylene terephthlate. Particular preference is given to cellulose fibers such as pulp. The fibers generally have a diameter of 1–200 µm, and preferably 10–100 µm, and also have a minimum length of 1 mm.

Diaper construction and shape is common knowledge and described for example in WO 95/26209 page 66 line 34 to page 69 line 11, DE 196 04 601 A1, EP-A-0 316 518 and EP-A-0 202 127. Diapers and other hygiene articles are generally also described in WO 00/65084, especially at pages 6–15, WO 00/65348, especially at pages 4–17, WO 00/35502, especially pages 3–9, DE 19737434, WO 98/8439. Hygiene articles for feminine hygiene are described in the following references. The inventive polymer mixtures capable of absorbing aqueous fluids can be used there. Femcare references: WO 95/24173: Absorption Article for Controlling Odour, WO 91/11977: Body Fluid Odour Control, EP 389023: Absorbent Sanitary Articles, WO 94/25077: Odour Control Material, WO 97/01317: Absorbent Hygienic Article, WO 99/18905, EP 834297, U.S. Pat. No. 5,762,644, U.S. Pat. No. 5,895,381, WO 98/57609, WO 2000/065083, WO 2000/069485, WO 2000/069484, WO 2000/069481, U.S. Pat. No. 6,123,693, EP 1104666, WO 2001/024755, WO 2001/000115, EP 105373, WO 2001/041692, EP 1074233. Tampons are described in the following references: WO 98/48753, WO 98/41179, WO 97/09022, WO 98/46182, WO 98/46181, WO 2001/043679, WO 2001/043680, WO 2000/061052, EP 1108408, WO 2001/033962, DE 200020662, WO 2001/001910, WO 2001/001908, WO 2001/001909, WO 2001/001906, WO 2001/001905, WO 2001/24729. Incontinence articles are described in the following references: Disposable Absorbent Article for Incontinent Individuals: EP 311344 description pages 3–9; Disposable Absorbent Article: EP 850623; Absorbent Article: WO 95/26207; Absorbent Article: EP 894502; Dry Laid Fibrous Structure: EP 850 616; WO 98/22063; WO 97/49365; EP 903134; EP 887060; EP 887059; EP 887058; EP 887057; EP 887056; EP 931530; WO 99/25284; WO 98/48753. Femcare and incontinence articles are described in the following references: Catamenial Device: WO 93/22998 description pages 26–33; Absorbent Members for Body Fluids: WO 95/26209 description pages 36–69; Disposable Absorbent Article: WO 98/20916 description pages 13–24; Improved Composite Absorbent Structures: EP 306262 description pages 3–14; Body Waste Absorbent Article: WO 99/45973. These references and the references therein are hereby expressly incorporated in the disclosure of the present invention.

Alternatively, the core (C) can also be composed of layers of the components (i) and (ii). It is in principle possible for multilayer constructions of 3 (eg layer of component (i)/layer of component (ii)/layer of component (i) or layer of component (ii)/layer of component (i)/layer of component (ii)), 4, 5 or more layers to be present, but preference is given to constructions having two layers, in which case not only the layer of component (i) but also the layer of component (ii) can be closer to the body. Other possibilities are layer constructions composed of layers comprising polymer mixtures according to the present invention and layers of individual components (i) and/or (ii).

The polymer mixtures according to the invention are very useful as absorbents for water and aqueous fluids, so that they may be used with advantage as a water retainer in market gardening, as a filter aid and particularly as an absorbent component in hygiene articles such as diapers, tampons or sanitary napkins.

Incorporation and Fixation of the Highly Swellable Polymer Mixtures According to the Invention In addition to the above-described polymer mixture of hydrogel-forming polymers and copolymers of $C_2$–$C_8$ olefins or styrenes with anhydrides, the absorbent composition of the present invention may include constructions which include the polymer mixture or to which they are fixed. Any construction is suitable that is capable of accommodating the polymer mixture and of being integrated into the absorption layer. A multiplicity of such compositions is already known and described in detail in the literature. A construction for installing the polymer mixture can be for example a fiber matrix consisting of a cellulose fiber mixture (air-laid web, wet laid web) or synthetic polymer fibers (meltblown web, spunbonded web) or else of a fiber blend of cellulose fibers and synthetic fibers. Possible fiber materials are detailed in the chapter which follows. The air-laid web process is described for example in WO 98/28 478. Furthermore, open-celled foams or the like may be used to install the polymer mixture according to the invention.

Alternatively, such a construction can be the result of fusing two individual layers to form one or better a multiplicity of chambers which contain the polymer mixture. Such a chamber system is described in detail in EP 0 615 736 A1 page 7 lines 26 et seq.

In this case, at least one of the two layers should be water pervious. The second layer may either be water pervious or water impervious. The layer material used may be tissues or other fabric, closed or open-celled foams, perforated films, elastomers or fabrics composed of fiber material. When the absorbent composition consists of a construction of layers, the layer material should have a pore structure whose pore dimensions are small enough to retain the particles of the polymer mixture. The above examples on the construction of the absorbent composition also include laminates composed of at least two layers between which the polymer mixture is installed and fixed.

Generally it is possible to fix the particles of the polymer mixture within the absorbent core to improve dry and wet integrity. Dry and wet integrity describes the ability to install highly swellable hydrogels into the absorbent composition in such a way that they withstand external forces not only in the wet but also in the dry state and highly swellable polymer does not dislocate or spill out. The forces referred to are especially mechanical stresses as occur in the course of moving about while wearing the hygiene article or else the weight pressure on the hygiene article in the case of incontinence especially. As to fixation, one skilled in the art knows a multiplicity of possibilities. Examples such as fixation by heat treatment, addition of adhesives, thermoplastics, binder materials are noted in WO 95/26 209 page 37 line 36 to page 41 line 14. The cited passage is thus part of this invention. Methods for enhancing wet strength are also to be found in WO 2000/36216 A1.

Furthermore, the absorbent composition may comprise a base material, for example a polymer film on which the polymer mixture is fixed. The fixing may be effected not only on one side but also on both sides. The base material can be water pervious or water impervious.

The above constructions of the absorbent composition incorporate particles of the polymer mixture at a weight fraction of from 10 to 100% by weight, preferably 20–100% by weight, more preferably 30–100% by weight, even more preferably 40–100% by weight, much more preferably 50–100% by weight, particularly preferably 60–100% by weight, especially preferably 70–100% by weight, extremely preferably 80–100% by weight and most preferably 90–100% by weight, based on the total weight of the construction and of the polymer mixture.

Fiber Materials of the Absorbent Composition

The structure of the present absorbent composition according to the invention may be based on various fiber materials, which are used as a fiber network or matrices. The present invention includes not only fibers of natural origin (modified or unmodified) but also synthetic fibers.

A detailed overview of examples of fibers which can be used in the present invention is given in WO 95/26 209 page 28 line 9 to page 36 line 8. The cited passage is thus part of this invention.

Examples of cellulose fibers include cellulose fibers which are customarily used in absorption products, such as fluff pulp and cellulose of the cotton type. The materials (soft- or hardwoods), production processes such as chemical pulp, semichemical pulp, chemothermo-mechanical pulp (CTMP) and bleaching processes are not particularly restricted. For instance, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent core, to continuously increase the fraction of thermoplastic fibers in the direction of the topsheet, which results in a similarly continuous increase in the pore sizes. Thermoplastic fibers can be formed from a multiplicity of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9 000 meters) in diameter may preferably be used. Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10 000 meters) is particularly preferred. The form of the fiber may vary; examples include woven types, narrow cylindrical types, cut/chopped yarn types, staple fiber types and continuous filament fiber types.

The fibers in the absorbent composition of the invention can be hydrophilic, hydrophobic or a combination thereof. According to the definition of Robert F. Gould in the 1964 American Chemical Society publication "Contact angle, wettability and adhesion", a fiber is referred to as hydrophilic when the contact angle between the liquid and the fiber (or the fiber surface) is less than 90° or when the liquid tends to spread spontaneously on the same surface. The two processes are generally coexistent. Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the polymer mixture. In the manufacturing process, layers having different hydrophilicities are used to create a gradient which channels impinging fluid to the hydrogel, where it is ultimately absorbed.

Suitable hydrophilic fibers for use in the absorbent composition of the invention include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophilicizing hydrophobic fibers, for example the treatment of thermoplastic fibers obtained from polyolefins (e.g. polyethylene or polypropylene, polyamides, polystyrenes, polyurethanes, etc.) with surfactants or silica. However, for cost reasons and ease of availability, cellulosic fibers are preferred.

The polymer mixture is embedded in the fibrous material described. This can be done in various ways, for example by using the polymer material and the fibers together to create an absorbent layer in the form of a matrix, or by incorporating the polymer particle mixture in layers of fiber mixture, where they are ultimately fixed, whether by means of adhesive or by lamination of the layers.

The fluid-acquiring and -distributing fiber matrix may comprise synthetic fiber or cellulosic fiber or a mixture of synthetic fiber and cellulosic fiber, in which case the mixing ratio may vary from (100 to 0) synthetic fiber: (0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include for example polyamide-epichlorohydrin coatings (Kymene® 557 H, Hercoles, Inc. Wilmington, Del.), polyacrylamide coatings (described in U.S. Pat. No. 3,556,932 or as the Parez® 631 NC commercial product from American Cyanamid Co., Stamford, Conn.), melamine-formaldehyde coatings and polyethyleneimine coatings.

Cellulosic fibers may also be chemically stiffened by chemical reaction. For instance, suitable crosslinker substances may be added to effect crosslinking taking place within the fiber. Suitable crosslinker substances are typical substances used for crosslinking monomers including but not limited to $C_2$–$C_8$-dialdehydes, $C_2$–$C_8$-monoaldehydes having acid functionality and in particular $C_2$–$C_9$-polycarboxylic acids. Specific substances from this series are for example glutaraldehyde, glyoxal, glyoxylic acid, formaldehyde and citric acid. These substances react with at least 2 hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162, U.S. Pat. No. 3,224,926, U.S. Pat. No. 3,440,135, U.S. Pat. No. 3,932,209, U.S. Pat. No. 4,035,147, U.S. Pat. No. 4,822,453, U.S. Pat. No. 4,888,093, U.S. Pat. No. 4,898,642 and U.S. Pat. No. 5,137,537. The chemical crosslinking imparts stiffening to the fiber material, which is ultimately reflected in improved dimensional stability for the hygiene article as a whole. The individual layers are joined together by methods known to one skilled in the art, for example intermelting by heat treatment, addition of hot-melt adhesives, latex binders, etc.

Methods of Making the Absorbent Composition

The absorbent composition is composed of constructions which include the polymer mixture and the polymer mixture which is resent in said constructions or fixed thereto.

Examples of processes to obtain an absorbent composition comprising for example a base material to which particles of the polymer mixture are fixed on one or both sides are known and included by the invention but not limited thereto.

Examples of processes to obtain an absorbent composition comprising for example polymer mixture (c) embedded in a fiber material blend of synthetic fibers (a) and cellulosic fibers (b), the blend ratio varying from (100 to 0) synthetic fiber: (0 to 100) cellulosic fiber, include (1) a process where (a), (b) and (c) are mixed together at one and the same time, (2) a process where a mixture of (a) and (b) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in, and (7) a process where (b) and (c) are mixed separately into (a). Of these examples, processes (1) and (5) are preferred. The apparatus used in this process is not particularly restricted and any customary apparatus known to one skilled in the art can be used.

The absorbent composition obtained in this way can optionally be subjected to a heat treatment, so that an absorption layer having excellent dimensional stability in the moist state is obtained. The heat treatment process is not particularly restricted. Examples include heat treatment by feeding hot air or infrared irradiation. The temperature of the heat treatment is in the range from 60° C. to 230° C., preferably from 100° C. to 200° C., particularly preferably from 100° C. to 180° C.

The duration of the heat treatment depends on the type of synthetic fiber, its amount and the hygiene article production rate. Generally the duration of the heat treatment is in the range from 0.5 second to 3 minutes, preferably from 1 second to 1 minute.

The absorbent composition is generally provided for example with a liquid-pervious topsheet and a liquid-impervious backsheet. Furthermore, leg cuffs and adhesive tabs are attached to finalize the hygiene article. The materials and types of pervious topsheet and impervious backsheet and of the leg cuffs and adhesive tabs are known to one skilled in the art and are not particularly restricted. Examples thereof may be found in WO 95/26 209.

Test Methods a) Centrifuge Retention Capacity (CRC)

This method measures the free swellability of the polymer mixture in a teabag. 0.2000±0.0050 g of the polymer mixture of the invention, e.g. dry polymer mixture, consisting of 0.18 g of hydrogel-forming polymer (particle size fraction 106–850 µm) and 0.02 g of copolymers of $C_2$–$C_8$ olefins or styrenes with anhydrides (particle size fraction 100–400 µm) are weighed into a teabag 60×85 mm in size which is subsequently sealed. The teabag is placed for 30 minutes in an excess of 0.9% by weight sodium chloride solution (at least 0.83 l of sodium chloride solution/1 g of polymer powder). The teabag is then centrifuged for 3 minutes at 250 g. The amount of liquid is determined by weighing back the centrifuged teabag.

To determine the CRC in the comparative tests the hydrogel-forming polymer was used alone in place of the polymer mixture (0.2000±0.0050 g).

b) Absorbency Under Load (AUL) (0.7 psi)

The measuring cell for determining AUL 0.7 psi is a Plexiglass cylinder 60 mm in internal diameter and 50 mm in height. Adhesively attached to its underside is a stainless steel sieve bottom having a mesh size of 36 µm. The measuring cell further includes a plastic plate having a diameter of 59 mm and a weight which can be placed in the measuring cell together with the plastic plate. The plastic plate and the weight together weigh 1 345 g. AUL 0.7 psi is determined by determining the weight of the empty Plexiglass cylinder and of the plastic plate and recording it as $W_0$. 0.900±0.005 g of a polymer mixture of the invention, eg polymer mixture consisting of 0.81 g of hydrogel-forming polymer (particle size fraction 106–850 µm) and 0.09 g of copolymers of $C_2$–$C_8$ olefins or styrenes with anhydrides (particle size fraction 100–400 µm) are then weighed into the Plexiglass cylinder and distributed very uniformly over the stainless steel sieve bottom. The plastic plate is then carefully placed in the Plexiglass cylinder, the entire unit is weighed and the weight is recorded as $W_a$. The weight is then placed on the plastic plate in the Plexiglass cylinder. A ceramic filter plate 120 mm in diameter and 0 in porosity is then placed in the middle of the Petri dish 200 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 µm in pore size (S&S 589 Schwarzband from Schleicher & Schüll) is subsequently placed on the ceramic plate. The Plexiglass cylinder containing the polymer mixture is then placed with plastic plate and weight on top of the filter paper and left there for 60 minutes. At the end of this period, the complete unit is removed from the filter paper and the Petri dish and subsequently the weight is removed from the Plexiglass cylinder. The Plexiglass cylinder containing swollen hydrogel mixture is weighed together with the plastic plate and the weight recorded as $W_b$.

AUL was calculated by the following equation:

$$AUL\ 0.7\ psi\ [g/g] = [W_b - W_a]/[W_a - W_0]$$

AUL 0.5 psi is measured using a correspondingly lighter weight on the plastic plate.

To determine AUL 0.7 psi and 0.5 psi, respectively, in the comparative tests the hydrogel-forming polymer was used alone in place of the polymer mixture (0.9000±0.005 g).

c) Saline Flow Conductivity (SFC)

The test method for determining SFC is described in U.S. Pat. No. 5,599,335.

d) pH Measurement of Hydrogel-Forming Polymers 100 ml of 0.9% by weight NaCl solution are magnetically stirred at moderate speed in a 150 ml beaker without air being drawn into the solution. This solution is admixed with 0.5±0.001 g of the polymer to be measured and stirred for 10 minutes. After 10 minutes, the pH of the solution is measured with a pH glass electrode, the value not being read off until it is stable, but at the earliest after 1 minute.

e) Measuring the Buffering Capacity of Hydrogel-Forming Polymers

To determine the buffering capacity of the hydrogel-forming polymers, 0.5±0.001 g of hydrogel-forming polymer or polymer mixture is placed in 100 ml of 0.9% by weight NaCl solution in a 150 ml glass beaker and magnetically stirred at moderate speed, so that the stirring does not draw any air into the solution.

After 10 minutes, the pH of the solution is measured for the first time with a pH glass electrode, the value not being read off until it is stable, but at the earliest after 1 minute. Subsequently, 0.1 molar NaOH solution is then added by 0.05 ml of 0.1 molar NaOH solution being metered in every 5 minutes with continued stirring. The pH of the mixture was continually checked in the course of the addition. The buffering capacity was determined from the pH prior to the addition of the 0.1 molar NaOH solution and from the pH after 6 hours.

EXAMPLES

The polymer mixtures obtained in the inventive examples are distinguished from the polymers obtained in the comparative examples by a combination of absorption quantity and swell rate and exhibit a high fluid permeability and also improved odor control properties. They are therefore very useful as absorbents for water and aqueous fluids, especially body fluids, for example urine or blood, for example in hygiene articles such as for example infant and adult diapers, sanitary napkins, tampons and the like.

The examples hereinbelow illustrate the invention.

Comparative Example 1 a) In a 40 l plastic bucket, 6.9 kg of glacial acrylic acid are diluted with 20 kg of deionized water. 33 g of pentaerythritol triallyl ether are added to this solution with stirring, and the sealed bucket is inertized by passing nitrogen through it. The polymerization is then initiated by adding 0.4 g of hydrogen peroxide dissolved in 40 ml of deionized water and 0.2 g of ascorbic acid dissolved in 40 ml of deionized water. After the reaction has ended, the gel is mechanically comminuted and mixed with sufficient aqueous sodium hydroxide solution for a degree of neutralization of 75 mol %, based on acrylic acid used. The neutralized gel is then dried on a can dryer, ground with a pin mill and finally screened off at 150–850 μm.

b) The base polymer prepared under a) was sprayed with 2.9% by weight of crosslinker solution composed of 49.56 parts by weight of 1,2-propanediol, 49.56 parts by weight of deionized water and 0.88 part by weight of monoethylene glycol diglycidyl ester (EDGE) in a Lödige laboratory mixer, the percentages being based on base polymer. The moist product was then transferred into a second preheated Lödige laboratory mixer and annealed at 140° C. for 60 minutes. The dried product was cooled down to room temperature and screened off at 850 μm.

Comparative Example 2 a) In a 40 l plastic bucket, 6.9 kg of glacial acrylic acid are diluted with 20 kg of deionized water. 33 g of pentaerythritol triallyl ether are added to this solution with stirring, and the sealed bucket is inertized by passing nitrogen through it. The polymerization is then initiated by adding 0.4 g of hydrogen peroxide dissolved in 40 ml of deionized water and 0.2 g of ascorbic acid dissolved in 40 ml of deionized water. After the reaction has ended, the gel is mechanically comminuted and mixed with sufficient aqueous sodium hydroxide solution for a degree of neutralization of 75 mol %, based on acrylic acid used. The neutralized gel is then dried on a can dryer, ground with a pin mill and finally screened off at 150–850 μm.

b) The base polymer prepared under a) was sprayed with 3.75% by weight of crosslinker solution composed of 33.3 parts by weight of 1,2-propanediol, 63.5 parts by weight of deionized water and 3.2 parts by weight of EDGE and also with 0.12 part by weight of a 27% aqueous aluminum sulfate solution in a Lödige laboratory mixer, the percentages being based on base polymer. Crosslinker solution and aluminum sulfate solution are sprayed separately but simultaneously from 2 nozzles. The moist product was then transferred into a second preheated Lödige laboratory mixer and annealed at 140° C. for 60 minutes. The dried product was cooled down to room temperature and screened off at 850 μm.

Comparative Example 3

A 10 l capacity polyethylene vessel thoroughly insulated with foamed plastic material is charged with 3 928 g of completely ion-free water, 625 g of sodium bicarbonate are suspended in the water and 2 000 g of acrylic acid are added with stirring so that there is no over-foaming due to ensuing $CO_2$ evolution. This is followed by the addition, in succession, of an emulsion of 1.3 g of sorbitan monococoate in 100 g of completely ion-free water and 8.1 g of allyl methacrylate, and the solution is further inertized by passing nitrogen into it. This is followed by the addition of the initiator system, consisting of 1.66 g of 2,2'-azobisamidinopropane dihydrochloride (dissolved in 20 g of completely ion-free water), 3.33 g of potassium peroxodisulfate (dissolved in 150 g of completely ion-free water) and also 0.3 g of ascorbic acid (dissolved in 25 g of completely ion-free water) in succession with stirring. The reaction solution is then left to stand without stirring. The polymerization which ensues, and in the course of which the temperature rises to about 90° C., produces a solid gel. This solid gel is mechanically comminuted using a meat grinder, dried on VA stainless steel wire mesh in a circulating air drying cabinet at 160° C., then ground and screened.

Comparative Example 4

TYLOSE VS 3790, a superabsorbent from CASSELLA AG of Frankfurt/Main, characterized by a pH of 5–5.5, prepared similarly to example 7 of EP 0 316 792 B1, was admixed on a 20 g scale in a WARING blender (modified attachment for kitchen processor) with a surface-postcrosslinking solution (spray from 2 ml syringe), consisting of 2.3% of water/1.2% of 1,2-propanediol/0.2% of ethylene glycol diglycidyl ether (each percentage being based on polymer) and heat treated in a circulating air drying cabinet at 140° C. for one hour.

Comparative Example 5

A WERNER & PFLEIDERER laboratory kneader having a working capacity of 2 l is evacuated to 980 mbar absolute by means of a vacuum pump and a previously separately prepared monomer solution which has been cooled to about 25° C. and inertized by passing nitrogen into it is sucked into the kneader. The monomer solution has the following composition: 825.5 g of completely ion-free water, 431 g of acrylic acid, 120.68 g of 50% NaOH, 0.86 g of polyethylene glycol 400 diacrylate (SARTOMER® 344 from CRAY VALLEY). To improve the inertization, the kneader is evacuated and subsequently refilled with nitrogen. This operation is repeated 3 times. A solution of 1.2 g of sodium persulfate (dissolved in 6.8 g of completely ion-free water) is then sucked in, followed after a further 30 seconds by a further solution consisting of 0.024 g of ascorbic acid dissolved in 4.8 g of completely ion-free water. After a nitrogen purge a preheated jacket heating circuit on bypass at 75° C. is switched over to the kneader jacket and the stirrer speed increased to 96 rpm. After ensuing polymerization and the attainment of $T_{max}$, the jacket heating circuit is reswitched back to bypass, and the batch is supplementarily polymerized for 15 minutes without heating/cooling, subsequently cooled and discharged. The resultant gel particles are dried at 160° C. on wire mesh bottomed trays in a circulating air drying cabinet and then ground and screened.

1 200 g of the thus obtained product of the particle size distribution 105–850 μm were sprayed with a homogeneous solution consisting of 17.58 g of water, 9.96 g of 1,2-propanediol, 1.2 g of ethylene glycol diglycidyl ether and 3.36 g of 26.8% aqueous aluminum sulfate solution in a powder mixing assembly (Lödige mixer) and transferred into a second, preheated Lödige mixer. The heat treatment was carried out for a period of 70 minutes under constant conditions of 150° C. jacket temperature and stirrer speed 60 rpm. The mixer was emptied, the product was cooled to room temperature and screened off at 850 μm.

Inventive Example 1

5 parts of powder of the 1/1 i-butylene/maleic anhydride copolymer from Kuraray Isoprene Chemical Company, Ltd., (Tokyo, Japan, trade name: ISOBAM®) and 95 parts from comparative example 4 are mixed in a laboratory tumble mixer for 60 minutes until homogeneous.

Inventive Example 2

10 parts of powder of the 1/1 i-butylene/maleic anhydride copolymer from Kuraray Isoprene Chemical Company, Ltd., (Tokyo, Japan, trade name: ISOBAM®) and 90 parts from comparative example 4 are mixed in a laboratory tumble mixer for 60 minutes until homogeneous.

Inventive Example 3

5 parts of powder of the 1/1 i-butylene/maleic anhydride copolymer from Kuraray Isoprene Chemical Company, Ltd., (Tokyo, Japan, trade name: ISOBAM®) and 95 parts from comparative example 2 are mixed in a laboratory tumble mixer for 60 minutes until homogeneous.

Inventive Example 4

10 parts of powder of the 1/1 i-butylene/maleic anhydride copolymer from Kuraray Isoprene Chemical Company, Ltd., (Tokyo, Japan, trade name: ISOBAM®) and 90 parts from comparative example 2 are mixed in a laboratory tumble mixer for 60 minutes until homogeneous.

Inventive Example 5

50 parts of powder of the i-butylene/maleic anhydride copolymer fibers prepared as per the method of U.S. Pat. No. 5,026,784 Example 1 column 8 line 24 and 50 parts from comparative example 1 are mixed in a laboratory tumble mixer for 60 minutes until homogeneous.

The absorptive performance data of the examples are discernible from table 1, while the odor control properties are approximated in table 2 using the pH as measured after 6 hours (buffering capacity).

TABLE 1

| Example | pH | SFC ×10$^{-7}$ cm$^3$s/g | CRC g/g | AUL 0.5 psi g/g | AUL 0.7 psi g/g |
|---|---|---|---|---|---|
| Comparative 1 | 5.95 | 5 | 33.4 | 29.4 | 22.8 |
| Comparative 2 | 6.1 | 15 | 29 | 26 | 23 |
| Comparative 3 | 4.5 | 3 | 23 | 11 | 7 |
| Comparative 4 | 5.4 | ≦1 | 42.0 | | 6.0 |
| Comparative 5 | 4.47 | 13.8 | 20.7 | | 18.1 |
| Inventive 1 | 5.4 | 9 | 42.0 | | 6.1 |
| Inventive 2 | 5.4 | 14 | 40.8 | | 5.9 |
| Inventive 3 | 6.1 | 18 | 28.7 | 25.5 | 23 |
| Inventive 4 | 6.1 | 24 | 28.9 | 25.9 | 22.3 |
| Inventive 5 | 6.4 | ≦1 | 41.8 | 28.7 | 20.2 |

TABLE 2

| Example | pH | pH after 6 hours (buffering capacity) |
|---|---|---|
| Comparative 1 | 5.95 | 6.6 |
| Comparative 2 | 6.1 | 7.1 |
| Comparative 3 | 4.5 | 4.7 |
| Comparative 5 | 4.47 | 4.6 |
| Inventive 1 | 5.4 | 5.5 |
| Inventive 2 | 5.4 | 5.4 |
| Inventive 3 | 6.1 | 6.2 |
| Inventive 4 | 6.1 | 5.9 |

The results show that the inventive examples provide distinctly improved odor control coupled with substantially the same absorptive performance. The distinctly improved odor control was demonstrated in the test by the enormous buffering capacity on titration with 0.1 molar NaOH solution. Comparative example 3 and comparative example 5 admittedly likewise give good odor control at a lower pH than inventive examples 1 and 2, but the performance with regard to CRC in particular is distinctly worse.

Comparative examples 1 and 2 are each a hydrogel-forming material from the prior art, which has been optimized especially with regard to Absorbency Under Load at pH 5.95 and pH 6.1 respectively, whereas the odor control properties (buffering capacity) are moderate. However, mixing this material with copolymer fibers (in a ratio of 1:1 in comparative example 1) gives increased retention values.

We claim:

1. A polymer mixture including components (i) a hydrogel-forming polymer capable of absorbing aqueous fluids and prepared by polymerizing an olefinically unsaturated carboxylic acid or a derivative thereof, and (ii) a copolymer of a $C_2$–$C_8$ olefin or styrene with an anhydride in a molar ratio between the $C_2$–$C_8$ olefin or styrene and the anhydride in a range from 3:1 to 1:3.

2. The polymer mixture of claim 1 wherein component (i) is granular or fibrous, and component (ii) is independently granular or fibrous, and optionally component (ii) is additionally fibrous or granular.

3. The polymer mixture of claim 1 wherein component (ii) is sprayed onto component (i) as a polymer or as a monomer mixture with subsequent polymerization.

4. The polymer mixture of claim 1 wherein component (i) comprises a polyacrylate.

5. The polymer mixture of claim 1 wherein component (ii) is granular.

6. The polymer mixture of claim 1 wherein component (ii) is unhydrolyzed.

7. The polymer mixture of claim 1 wherein the anhydride component of component (ii) is maleic anhydride and the olefinic or styrene component is selected from one or more of isobutylene, vinyl acetate, ethylene, and styrene.

8. The polymer mixture of claim 1 wherein component (i) is a grafted product.

9. The polymer mixture of claim 8 wherein component (i) is grafted onto carboxymethylcellulose.

10. The polymer mixture of claim 1 wherein component (i) is present in a fraction in a range from 99.7% by weight to 85% by weight, and component (ii) is present in a fraction in a range from 0.3% by weight to 15% by weight.

11. A hygiene article comprising a polymer mixture of claim 1.

12. A method of absorbing an aqueous fluid and reducing odor formation comprising contacting the fluid with a polymer mixture of claim 1.

* * * * *

UNITED STATES PATENT AND TRADEMARK OFFICE
CERTIFICATE OF CORRECTION

PATENT NO.        : 7,132,479 B2
APPLICATION NO.   : 10/505189
DATED             : November 7, 2006
INVENTOR(S)       : Friedrich Engelhardt et al.

It is certified that error appears in the above-identified patent and that said Letters Patent is hereby corrected as shown below:

On the Title Page:

Item (30), "102 10 124" should be -- 102 10 124.8 --.

Signed and Sealed this

Thirteenth Day of March, 2007

JON W. DUDAS
*Director of the United States Patent and Trademark Office*